(12) United States Patent
Kumar et al.

(10) Patent No.: US 9,155,872 B2
(45) Date of Patent: Oct. 13, 2015

(54) DRUG DELIVERY DEVICE FOR OVARIAN CANCER

(75) Inventors: Arun Kumar, Newark, DE (US);
Susana K. Lai-Yuen, Tampa, FL (US);
Shyam S. Mohapatra, Lutz, FL (US)

(73) Assignee: University of South Florida, Tampa, FL (US)

( * ) Notice: Subject to any disclaimer, the term of this patent is extended or adjusted under 35 U.S.C. 154(b) by 520 days.

(21) Appl. No.: 13/486,540

(22) Filed: Jun. 1, 2012

(65) Prior Publication Data

US 2013/0144163 A1 Jun. 6, 2013

Related U.S. Application Data

(63) Continuation of application No. PCT/US2010/058565, filed on Dec. 1, 2010.

(60) Provisional application No. 61/265,576, filed on Dec. 1, 2009.

(51) Int. Cl.
*A61M 5/315* (2006.01)
*A61M 31/00* (2006.01)
*A61B 17/43* (2006.01)

(52) U.S. Cl.
CPC ............. *A61M 31/00* (2013.01); *A61B 17/43* (2013.01); *A61M 2210/1408* (2013.01); *A61M 2210/1425* (2013.01)

(58) Field of Classification Search
CPC ............. A61M 2210/14; A61M 2210/1408; A61M 2210/1425; A61M 2210/1433; A61M 2210/1475; A61M 3/0204; A61M 3/0279; A61M 3/0283; A61M 31/00; A61M 5/31596; A61M 2005/31598; A61M 2005/1787; A61M 31/002; A61B 17/43

USPC .......... 604/158, 159, 164.01, 164.02, 164.08, 604/164.07, 164.09, 164.11, 164.12, 604/170.02, 73, 94.01, 93.01

See application file for complete search history.

(56) References Cited

U.S. PATENT DOCUMENTS 3,921,641 A 11/1975 Hulka
RE29,207 E 5/1977 Bolduc et al.
(Continued)

FOREIGN PATENT DOCUMENTS

WO 2009095912 A1 8/2009

OTHER PUBLICATIONS

International Search Report for International Application No. PCT/US2010/058565, filing date Dec. 1, 2010. Date of Mailing Aug. 18, 2011.
Hussain, A. and F. Ahsan, The vagina as a route for systemic drug delivery. Journal of Controlled Release, 2005. 103(2): pp. 301-313.
(Continued)

*Primary Examiner* — Bhisma Mehta
*Assistant Examiner* — Hamza Darb
(74) *Attorney, Agent, or Firm* — Michele L. Lawson; Smith & Hopen, P.A.

(57) ABSTRACT

A drug delivery device has been designed to directly deliver an agent to the ovaries through direct contact with the fallopian tubes. The device consists of three main components: a tubular inserter, a cylindrical chamber and a plunger. The device is a single-use applicator designed in a shape similar to a tampon to facilitate its insertion through the vagina and into the uterus. Positioning of the device centrally in the uterus is accomplished through the use of ultrasound. The chamber is inserted into the tubular inserter. Adjusting the length of the chamber inserted into the tubular inserter controls the amount of tubing released from the apertures in the tubular inserter. Ultrasound is used to ensure the proper placement of each tube at the entrance of each fallopian tube. The plunger is inserted into the chamber and adjustment of the plunger controls the amount of the agent released into the tubes.

20 Claims, 6 Drawing Sheets

(56) References Cited

U.S. PATENT DOCUMENTS

| | | | |
|---|---|---|---|
| 4,318,405 A | | 3/1982 | Sneider |
| 4,536,178 A | | 8/1985 | Lichstein et al. |
| 4,620,534 A | | 11/1986 | Zartman |
| 5,273,521 A | | 12/1993 | Peiler et al. |
| 5,330,427 A | | 7/1994 | Weissenburger |
| 5,382,252 A | | 1/1995 | Failla et al. |
| 5,419,777 A | * | 5/1995 | Hofling .................. 604/264 |
| 5,487,377 A | | 1/1996 | Smith et al. |
| 5,558,631 A | | 9/1996 | Campion et al. |
| 5,891,457 A | | 4/1999 | Neuwirth |
| 6,416,779 B1 | | 7/2002 | D'Augustine et al. |
| 6,423,038 B1 | | 7/2002 | Vancaillie |
| 6,423,075 B1 | | 7/2002 | Singh et al. |
| 6,802,825 B2 | | 10/2004 | Ackerman et al. |
| 7,104,968 B2 | | 9/2006 | Swick |
| 7,591,808 B2 | | 9/2009 | DiPiano et al. |
| 2005/0020997 A1 | | 1/2005 | Vancaillie |
| 2005/0240211 A1 | * | 10/2005 | Sporri et al. ................. 606/193 |
| 2006/0142794 A1 | | 6/2006 | Lendlein et al. |
| 2008/0097469 A1 | | 4/2008 | Gruber et al. |
| 2011/0014181 A1 | * | 1/2011 | Thornton .................. 424/130.1 |

OTHER PUBLICATIONS

Alexander, N. J., Baker, E., Kaptein, M., Karck, U., Miller, L., Zampaglione, E., Why consider vaginal drug administration? Fertility and Sterility, Jul. 2004. 82(1): p. 1-12.

Mary Justin-Temu, Ph.D., Festo Damian, Ph.D.; Renaat Kinget, Ph.D.; Guy Van Den Mooter, Ph.D., Intravaginal Gels as Drug Delivery Systems. Journal of Women's Health, vol. 13, No. 7, 2004, pp. 834-844.

Illum L., Nasal drug delivery: new developments and strategies. Drug Discovery Today. vol. 7, No. 23, 2002. pp. 1184-1189.

Merkus F.W.H.M., et al. Cyclodextrins in nasal drug delivery. Advanced Drug Delivery Reviews. vol. 36, 1999. pp. 41-57.

Langer R., Where a pill won't reach. Scientific American. 2003. vol. 288. pp. 50-57.

McAllister D.V., Allen M.G., and Prausnitz M.R., Microfabricated Microneedles for Gene and Drug Delivery. Annu Rev Biomed Eng. 2000; 2: pp. 289-313.

Henry S., McAllister D.V., Allen M.G., and Prausnitz M.R., Microfabricated Microneedles: A Novel Approach to Transdermal Drug Delivery. J Pharm Sci. vol. 87, No. 8, Aug. 1998. pp. 922-925.

Knuppel, R. A., Quantitive Transcervical Uterine Cultures with a new Device, Obstetrics and Gynecology, 1981, 57(2): pp. 243-248.

* cited by examiner

DRUG DELIVERY DEVICE FOR OVARIAN CANCER

CROSS REFERENCE TO RELATED APPLICATIONS

This application is a continuation of and claims priority to prior filed International Application No. PCT/US10/58565, entitled "Drug Delivery Device For Ovarian Cancer" filed Dec. 1, 2010, which claims priority to U.S. Provisional Patent Application No. 61/265,576 entitled "Drug Delivery Device For Ovarian Cancer" filed Dec. 1, 2009, which are herein incorporated by reference.

FIELD OF INVENTION

This invention relates to drug delivery devices. Specifically, the invention provides a direct drug delivery device to deliver an agent to the ovaries.

BACKGROUND OF THE INVENTION

The development of effective devices that can transport and deliver a drug precisely and safely to its target is a major challenge in the drug delivery field. New delivery technologies are developed each year that target nearly every part of the human body as potential routes for administering established and new drugs. These novel drug delivery technologies include nasal systems, transdermal patches, implants, and micro- and nano-devices.

The main goal of drug delivery systems is to deliver the drug to the target location at the required level in a safe and reproducible manner. There are many routes for administering drugs; the oral route is the most common and preferred method for drug delivery as it is non-invasive. However, the drug is gradually lost through the metabolism as it travels through the liver, stomach, and intestine. Other commonly used routes are the nasal drug delivery and injection. (Illum L. Nasal drug delivery: new developments and strategies. Drug Discovery Today. 2002; 7: 1184-1189; Merkus FWHM, et al. Cyclodextrins in nasal drug delivery. Adv Drug Deliv Rev. 1999; 36: 41-57). The nasal delivery shows poor absorption of polar compounds and the injection approach is normally associated with pain so patients tend to avoid this method. (Illum L. Nasal drug delivery: new developments and strategies. Drug Discovery Today. 2002; 7: 1184-1189). Transdermal techniques have also been proposed to deliver the drug to the bloodstream through the skin. (Langer R. Where a pill won't reach. Sci Am. 2003; 288: 50-57; McAllister D V, Allen M G, and Prausnitz M R. Microfabricated microneedles for gene and drug delivery. Annu Rev Biomed Eng. 2000; 2: 289-313; Henry S, McAllister D V, Allen M G, and Prausnitz M R. Microfabricated microneedles: a novel approach to transdermal drug delivery. J Pharm Sci. 1998; 87: 922-925).

According to the National Cancer Institute, ovarian cancer is accountable for the highest mortality rates of all gynecologic cancers. It is estimated that more than 21,000 new cases will be diagnosed and approximately 15,000 deaths will occur from ovarian cancer in 2009 in the U.S. Once ovarian cancer is detected, there are several treatments available that include surgery, radiation, and systemic chemotherapies. The major drawback of most current treatments with the exception of surgery is that they tend to kill the normal cells and tissues along with the cancerous cells throughout the body. Currently, surgery to remove the ovaries is considered the most effective treatment. However, the removal of ovaries can lead to side effects as ovaries are responsible for producing the female hormones that are important to a woman's health.

Most anticancer drugs are given via oral or injection methods. These drug delivery approaches can kill normal cells and tissues or lead to the gastrointestinal absorption of the drug before reaching the ovaries and areas within the pelvic cavity thus diminishing the effectiveness of the drugs.

Studies are exploring the potential of using the vagina as an alternative route for drug delivery. There are several factors that need to be taken into consideration when using the vagina as a route for drug delivery such as the drug formulation, age, hormone status, pH, and vaginal fluids (Hussain, A. and F. Ahsan, *The vagina as a route for systemic drug delivery*. J Control Release, 2005. 103(2): p. 301-13; Alexander, N. J., et al., *Why consider vaginal drug administration? Feral Steril*, 2004. 82(1): p. 1-12). When these factors are taken into consideration, advantages of using the vaginal route include: localized drug delivery, ease of administration, and by-passing the first metabolic reactions (Justin-Temu, M. D., Festo; Kinget, Renaat; Van Den Mooter, Guy, *Intravaginal Gels as Drug Delivery Systems*. Women's Health, 2004. 13).

The main goal of the medical device of the present invention is to transport and deliver a drug directly to the ovaries at the required level in a safe and non-invasive manner. The delivery of the drug directly to the ovaries enables a high concentration of the drug to reach the target location thus increasing the effectiveness of the drug on the patient. The direct delivery of drug via this device can also minimize dosage frequency and drug side effects. The device can be used for targeted drug delivery for the treatment of ovarian cancer, as well as for targeted sperm delivery and treating bacterial infection and inflammation.

SUMMARY OF INVENTION

In an embodiment of the present invention the drug delivery device is comprised of: a tubular inserter having a first insertion end and a first opposing end; a cylindrical chamber having a second insertion end and a second opposing end with the chamber being slidably received and retained within the first opposing end of the tubular inserter; and a plunger having a third insertion end and a third opposing end with the plunger being slidably received and retained within the second opposing end of the cylindrical chamber. A pair of apertures is disposed in the first insertion end of the tubular inserter. At least one tubing channel is also disposed within the first insertion end of the tubular inserter with the at least one channel terminating at the pair of apertures. A pair of tubes is disposed in the at least one tubing channel.

The device can be further comprised of a tube extension system selected from the group consisting of a full chamber tubing system; reinforced tubing extension system; a disc extension system; and a cylindrical chamber tube extension system.

The full chamber tubing system is comprised of the pair of tubes being disposed on the second flange of the cylindrical chamber. The pair of tubes extends from the flange through the length of the chamber, into the tubing channels and out of the apertures.

The reinforced tubing extension system is further comprised of a section of the pair of tubes extending from the at least one tubing channel being substantially rigid and capable of making contact with the second insertion end of the cylindrical chamber.

The disc extension system is further comprised of a disc having a first and a second side; a pair of apertures extending from the first side of the disc to the second side of the disc; a pair of tubes extending from the apertures on the second side of the disc into the at least one tubing channel; and a pin extending from the first side of the disc. The second side of the disc is in contact with the second insertion end of the cylindrical chamber.

The cylindrical chamber tube extension system is comprised of the pair of tubes disposed in the at least one tubing channel also being disposed on the second insertion end of the cylindrical chamber.

The tubular inserter can be further comprised of a first flange disposed at the first opposing end of the tubular inserter. A first opening can be disposed in the first flange to receive the second insertion end of the cylindrical chamber.

The cylindrical chamber can be further comprised of a second flange disposed at the second opposing end of the cylindrical chamber. A second opening can be disposed in the second flange to receive the third insertion end of the plunger.

The plunger may contain a dispensing compartment disposed at the third insertion end which holds the agent to be delivered.

The pair of tubes can be substantially longer in length than the at least one tubing channel. The tubular inserter can be generally cylindrical with the first insertion end of the inserter being rounded. The apertures can be positioned on opposing sides of the first insertion end of the tubular inserter.

In use, sliding the chamber in the inserter controls the amount of tubing which is released from the apertures while sliding the plunger within the chamber controls the release of the agent into the tubes and ultimately into the fallopian tubes and ovaries.

In another embodiment, the drug delivery device is comprised of: a tubular inserter having a first insertion end and a first opposing end; a cylindrical chamber having a second insertion end and a second opposing end with the chamber being slidably received and retained within the first opposing end of the tubular inserter; and a plunger having a third insertion end and a third opposing end with the plunger being slidably received and retained within the second opposing end of the cylindrical chamber. A pair of apertures is disposed in the first insertion end of the tubular inserter. A pair of tubing channels is also disposed within the first insertion end of the tubular inserter with the each channel terminating at one of the pair of apertures. A pair of tubes wherein each tube is disposed in one of the tubing channels.

The device can be further comprised of a tube extension system selected from the group consisting of a reinforced tubing extension system; a disc extension system; and a cylindrical chamber tube extension system.

The full chamber tubing system is comprised of the pair of tubes being disposed on the second flange of the cylindrical chamber. The pair of tubes extends from the flange through the length of the chamber, into the tubing channels and out of the apertures.

The reinforced tubing extension system is further comprised of a section of the pair of tubes extending from each of the tubing channels being substantially rigid and capable of making contact with the second insertion end of the cylindrical chamber.

The disc extension system is further comprised of a disc having a first and a second side; a pair of apertures extending from the first side of the disc to the second side of the disc; a pair of tubes extending from the apertures on the second side of the disc into the at least one tubing channel; and a pin extending from the first side of the disc. The second side of the disc is in contact with the second insertion end of the cylindrical chamber.

The cylindrical chamber tube extension system is comprised of the pair of tubes disposed in the tubing channels also being disposed on the second insertion end of the cylindrical chamber.

The tubular inserter can be further comprised of a first flange disposed at the first opposing end of the tubular inserter. A first opening can be disposed in the first flange to receive the second insertion end of the cylindrical chamber.

The cylindrical chamber can be further comprised of a second flange disposed at the second opposing end of the cylindrical chamber. A second opening can be disposed in the second flange to receive the third insertion end of the plunger.

The plunger may contain a dispensing compartment disposed at the third insertion end which holds the agent to be delivered.

The pair of tubes can be substantially longer in length than the tubing channels. The tubular inserter can be generally cylindrical with the first insertion end of the inserter being rounded. The apertures can be positioned on opposing sides of the first insertion end of the tubular inserter.

In use, sliding the chamber in the inserter controls the amount of tubing which is released from the apertures while sliding the plunger within the chamber controls the release of the agent into the tubes and ultimately into the fallopian tubes and ovaries.

In a further embodiment, the drug delivery device is comprised of: a tubular inserter having a first insertion end and a first opposing end; at least one aperture disposed in the first insertion end; at least one channel disposed in the first insertion end of the tubular inserter with the channel terminating at the aperture; and a plunger slidably received within the first opposing end of the tubular inserter.

The device can be further comprised of at least one tube being disposed in the at least one channel with the at least one tube being substantially longer than the at least one channel.

In another embodiment, a drug delivery system is presented. The drug delivery system is comprised of: a drug delivery device; an ultrasound device; and an agent. The drug delivery device is further comprised of: a tubular inserter having a first insertion end and a first opposing end; a cylindrical chamber having a second insertion end and a second opposing end with the chamber being slidably received and retained within the first opposing end of the tubular inserter; and a plunger having a third insertion end and a third opposing end with the plunger being slidably received and retained within the second opposing end of the cylindrical chamber. A pair of apertures is disposed in the first insertion end of the tubular inserter. At least one tubing channel is also disposed within the first insertion end of the tubular inserter with the at least one channel terminating at the pair of apertures. A pair of tubes is disposed in the at least one tubing channel with the tubes being substantially longer than the at least one tubing channel. A dispensing compartment can optionally be disposed at the third insertion end of the plunger.

The drug delivery device can be further comprised of a tube extension system selected from the group consisting of a reinforced tubing extension system; a disc extension system; and a cylindrical chamber tube extension system.

The full chamber tubing system is comprised of the pair of tubes being disposed on the second flange of the cylindrical chamber. The pair of tubes extends from the flange through the length of the chamber, into the tubing channels and out of the apertures.

The reinforced tubing extension system is further comprised of a section of the pair of tubes extending from the at least one tubing channel being substantially rigid and capable of making contact with the second insertion end of the cylindrical chamber.

The disc extension system is further comprised of a disc having a first and a second side; a pair of apertures extending from the first side of the disc to the second side of the disc; a pair of tubes extending from the apertures on the second side of the disc into the at least one tubing channel; and a pin extending from the first side of the disc. The second side of the disc is in contact with the second insertion end of the cylindrical chamber.

The cylindrical chamber tube extension system is comprised of the pair of tubes disposed in the at least one tubing channel also being disposed on the second insertion end of the cylindrical chamber.

In use, the ultrasound device assists in positioning the drug delivery device in the uterus. The agent is loaded into the drug delivery device and the drug delivery device is then used to release the therapeutic agent into the reproductive system.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
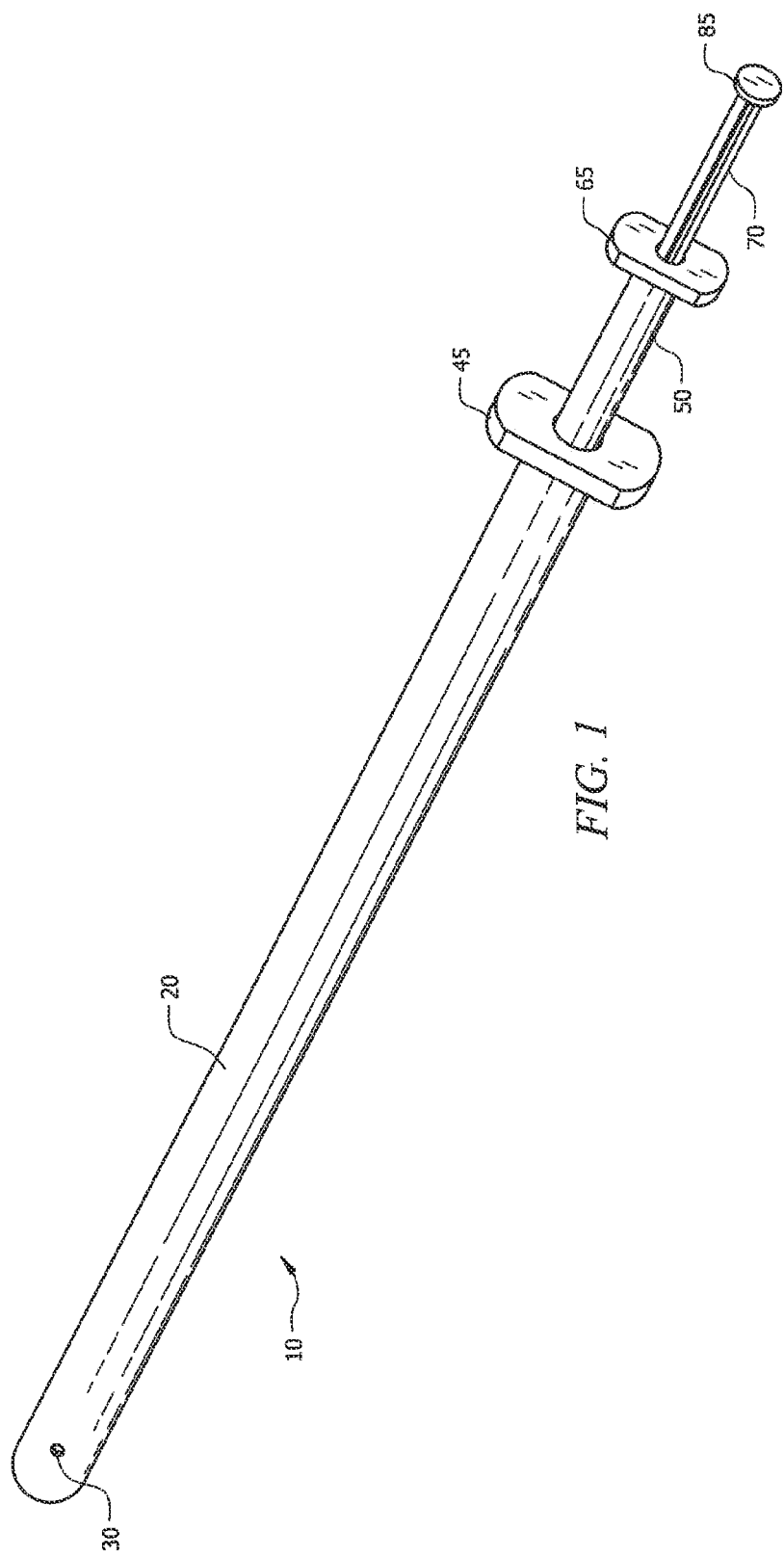
FIG. 1 is an image of an embodiment of the drug delivery device for ovarian cancer as assembled. The device consists of (1) a tubular inserter which is inserted into the uterus through the vagina; (2) a hollow cylindrical chamber which is inserted into the tubular inserter and functions to control the amount of tubing which is released from the device into the fallopian tubes; and (3) a plunger which controls the release of an agent.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

A new medical device 10 has been designed to directly deliver an agent 90 to the ovaries. The single-use device 10 directly transports and delivers an agent 90 to the entrance of the fallopian tubes in a non-invasive manner. The device 10 is a single-use applicator designed in a shape similar to a tampon to facilitate its insertion through the vagina and to reduce the patient's discomfort. It consists of three main components: the tubular inserter 20, the cylindrical chamber 50, and the plunger 70. The device 10 is inserted through the vagina and centrally positioned in the uterus using an ultrasound device to ensure correct positioning. A tube 60 extends from each side of the device 10 to the entrance of the fallopian tubes to facilitate delivery of an agent 90 directly to the ovaries. By applying the agent 90 at the entrance of the fallopian tubes, the agent 90 dissipates through the fallopian tubes and a higher concentration of the agent 90 is delivered to the target while virtually eliminating any amount of the agent 90 leaking out through the uterus and vagina.

Figure 2:
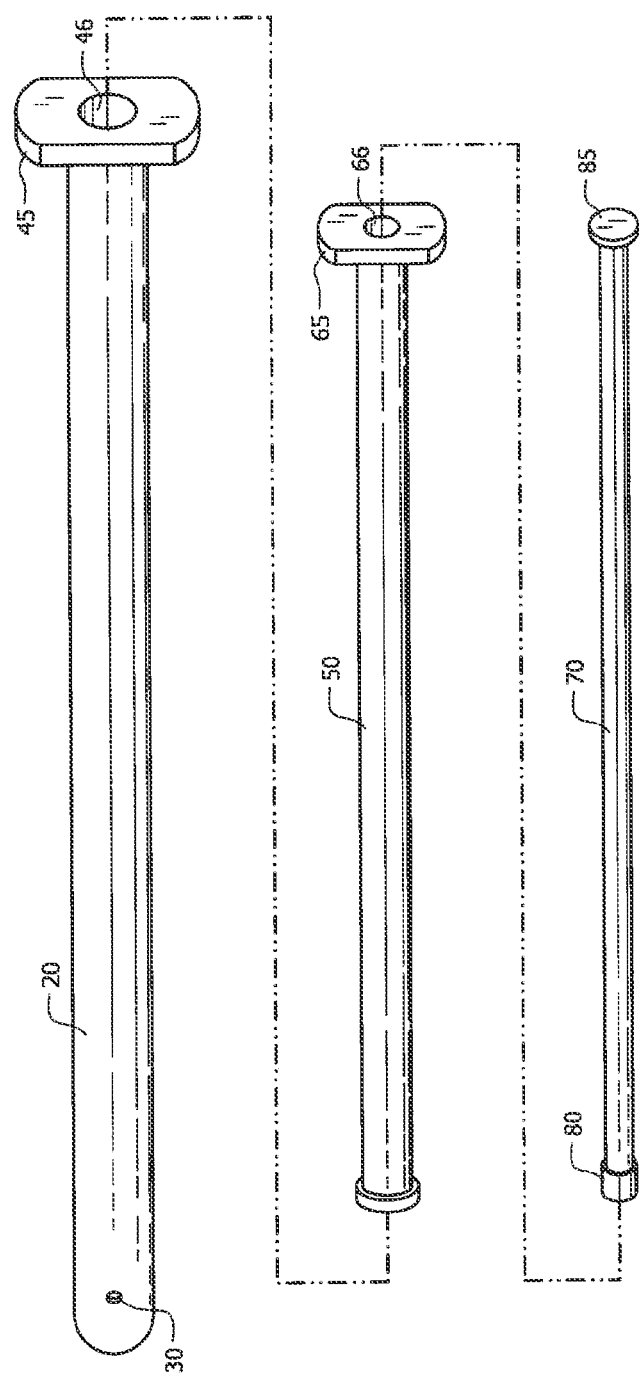
FIG. 2 is an image illustrating the interconnection of the main components of the device.
Figure 3:
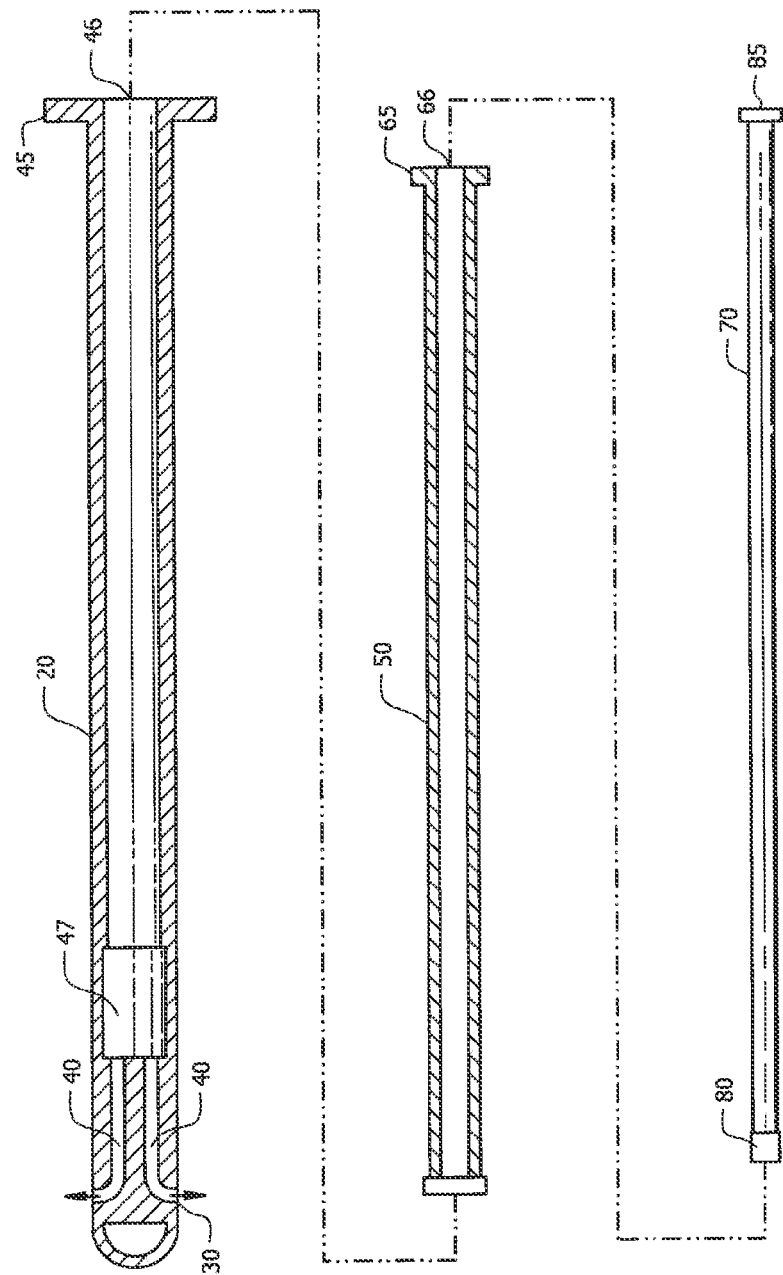
FIG. 3 is a cross-sectional image of each component of the device illustrating the interconnection of the components.

FIG. 1 illustrates an embodiment of the device 10 as assembled. FIG. 2 illustrates the interconnectivity of the three main components of the device 10. As shown, the tubular inserter 20 is generally cylindrical in shape and is of sufficient dimensions so as to be comfortably inserted into the uterus of a female. The first insertion end of the tubular inserter 20 is rounded and contains at least one aperture 30. The first opposing end of the inserter 20 contains a first flange 45 which functions to prevent the device 10 from being inserted too deeply into the uterus. This first opposing end of the tubular inserter 20 also has a first opening 46 disposed therein for the insertion of the cylindrical chamber 50.

As shown in the figures, the cylindrical chamber 50 is of a slightly smaller size and of sufficient dimension so as to be slidably received within the body of the tubular inserter 20. The second insertion end of the chamber 50 can be rounded and substantially closed with an opening in the center or a pair of openings corresponding roughly to the positioning of the tubes 60 and smaller in dimension than the width of the tubes 60 to allow the agent 90 to be dispensed into the channels 40 of the inserter 20 and ultimately into the fallopian tubes/ovaries. Alternatively, this second insertion end of the chamber 50 can have a pair of tubes 60 attached into which the agent 90 can be dispensed. The second opposing end of the chamber 50 has a second flange 65 to prevent the chamber 50 from being inserted too deeply into the tubular inserter 20; to allow for easy removal of the chamber 50 from the inserter 20; and to provide a grip for the adjustment of the chamber 50 within the inserter 20. The second opposing end of the chamber 50 also has a second opening 66 disposed therein to allow for the insertion of the plunger 70.

The plunger 70 is of slightly smaller size and sufficient dimension so as to be slidably received within the chamber 50. The main body of the plunger 70 can be of solid construction and generally cylindrical in shape. In an embodiment, the third insertion end of the plunger 70 can function as a syringe to push the agent 90 through the chamber 50 and into the tubes 60.

Alternatively, the third insertion end of the plunger 70 can contain a hollow dispensing compartment 80. This dispensing compartment 80 can contain the agent 90 for delivery to the fallopian tubes/ovaries. The dispensing compartment 80 can be manufactured of a material which can release the agent 90 contained therein when the compartment 80 is placed in contact with the second insertion end of the chamber 50. The third opposing end of the plunger 80 contains a third flange 85 which functions to prevent the plunger 80 from being inserted too deeply into the chamber 50; to allow easy removal of the plunger 80 from the chamber 50; to provide a grip for the adjustment of the plunger 80 within the chamber 50; and to control the dispensing of the agent 90.

FIGS. 3-7 illustrate cross sections of the main components of one embodiment of the device 10. As shown in the figures, the tubular inserter 20 is a generally cylindrical shaped elongated tube having a first insertion end and a first opposing end containing a first flange 45. The first insertion end is rounded and in use is inserted into the uterus of a female through the vagina. The first insertion end can contain a pair of apertures 30 with each aperture 30 being located on substantially opposite sides of the inserter 20.

Figure 6:
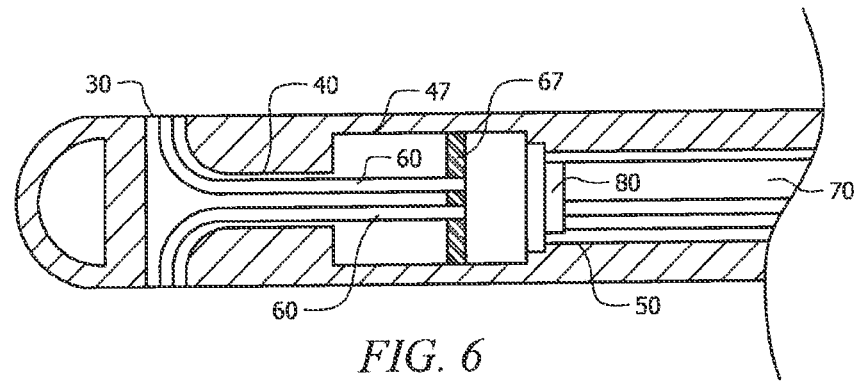
FIG. 6 is a cross-sectional image of the insertion end of the device illustrating the mechanism of delivery of the agent through the device to the fallopian tubes using the disc extension system. This figure also illustrates the single tubing channel which branches into a "T-shape".
Figure 7:
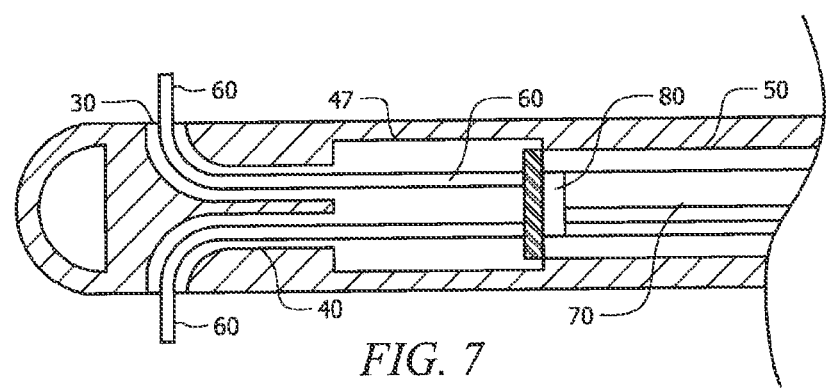
FIG. 7 is a cross-sectional image of the insertion end of the device illustrating the mechanism of delivery of the agent through the device to the fallopian tubes using the cylindrical chamber tube extension system

A tubing channel 40 can extend lengthwise from each aperture 30 to terminate in an area of working space 47. This area of working space 47 is a hollow area extending lengthwise through the main body of the tubular inserter 20 into which the cylindrical chamber 50 can be positioned to control the length of tubing 60 that is released into the tubing channels 40. The tubing channel 40 can be a singular central channel which branches as it approaches the apertures 30 to form a "T-shape" with each branch terminating at one of the apertures 30 as shown in FIG. 6. Alternatively, the tubing channel 40 can be two separate channels each of which extends from one of the apertures 30 downward to the working space 47 as shown in FIGS. 5 and 7.

In one embodiment, a pair of tubes 60 is disposed within the tubing channels 40. The tubes 60 can be substantially longer than the tubing channels 40. The term "substantially" as used with respect to the length of the tubing 60 means that the tubing 60 can be between 10% and 500% longer than the tubing channels 40. The tubes 60 can be part of a tube extension system which allows the tubes 60 to be moved within the tubing channels 40 so that the ends of the tubes 60 extend outwardly from the apertures 30 to reach the opening of the fallopian tubes. The tubing extension system can take many forms including but not limited to: a full chamber extension system; a reinforced tubing extension system; a disc extension system; and a cylindrical chamber tube extension system.

Figure 4:
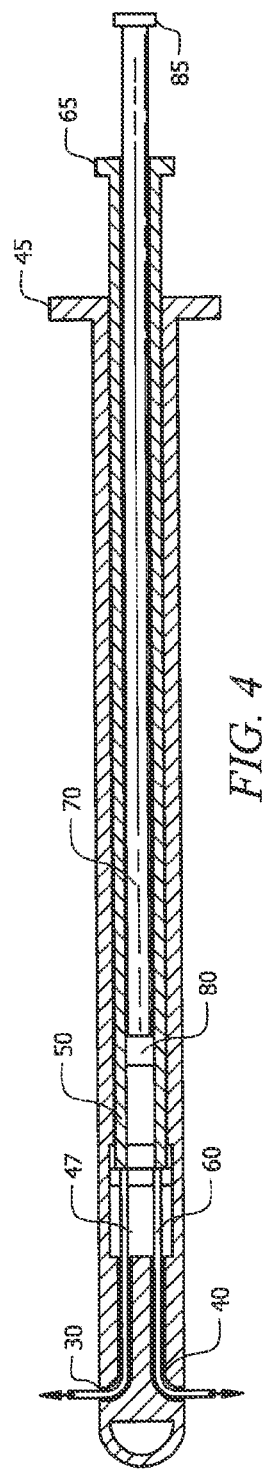
FIG. 4 is a cross sectional image of an embodiment of the fully assembled device illustrating one embodiment of the device with the pair of tubes attached at the flange of the chamber.

The full chamber extension system, as shown in FIG. 4, is comprised of the tubes 60 being attached to the second flange 65 of the cylindrical chamber 50. The tubes 60 extend from the second flange 65 of the chamber 50 through the length of the chamber 50 and out the first insertion end of the chamber 50 to enter the hollow working space 47. From here, the tubes 60 extend through the tubing channels 40 and out the apertures 30 to reach the fallopian tubes. Sliding the chamber 50 controls the amount of tubing 60 that is released from the apertures 30.

Figure 5:
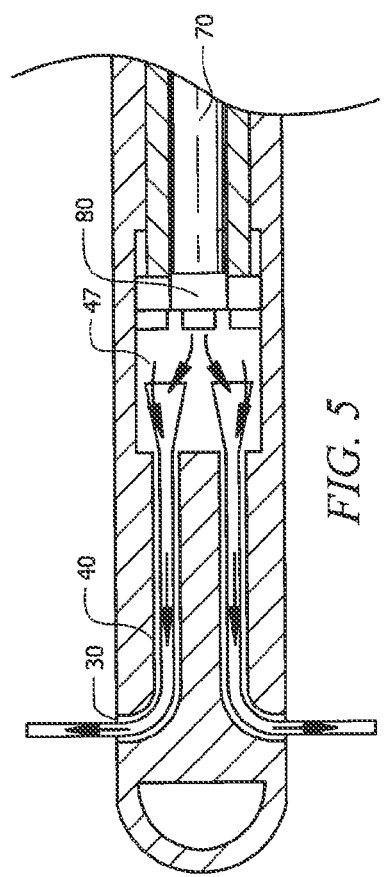
FIG. 5 is a cross-sectional image of the insertion end of the device illustrating the mechanism of delivery of the agent through the device to the fallopian tubes using the reinforced tubing extension system.

The reinforced tubing extension system, as shown in FIG. 5, is comprised of a section of the pair of tubes 60 extending from the tubing channels 40 being substantially rigid. The rigidity of this section of the tubes 60 allows the tubes 60 to be moved when the section is placed in contact with the second insertion end of the cylindrical chamber 50. The rigidity of this section of the tubes 60 allows the tubes 60 to move within the tubing channels 40 without collapsing at the tubing channel entrance. In operation, sliding the cylindrical chamber 50 telescopically within the tubular inserter 20 exerts pressure on this rigid section of the tubes 60 to move the tubes 60 within the working space 47 which in turn moves the tubes 60 through the tubing channel 40 and out of the apertures 30. Alternatively, the tubes 60 may extend through a single tubing channel 40 which branches into a "T-shape" as described above.

The disc extension system, as shown in FIG. 6 is comprised of a disc 67 having a first side and a second side; a pair of apertures extending from the first side of the disc to the second side of the disc 67; a pair of tubes 60 extending from the apertures on the second side of the disc 67 into the tubing channel 40; and a pin extending from the first side of the disc 67. The second side of the disc 67 is in contact with the second insertion end of the cylindrical chamber 50. In operation, sliding the cylindrical chamber 50 telescopically within the tubular inserter 20 exerts pressure on the disc 67 to move the disc 67 within the working space 47 which in turn moves the tubes 60 through the tubing channel 40 and out of the apertures 30. Alternatively, the tubes 60 may extend through two separate tubing channels 40 as described above.

The cylindrical chamber tube extension system, as shown in FIG. 7, is comprised of the pair of tubes 60 being disposed on the second insertion end of the cylindrical chamber 50. In operation, sliding the cylindrical chamber 50 telescopically within the tubular inserter 20 exerts pressure on the tubes 60 to move the tubes within the working space 47 which in turn moves the tubes through the tubing channels 40 and out of the apertures 30. Alternatively, the tubes 60 may extend through a single tubing channel 40 which branches into a "T-shape" as described above.

The tubes 60 can be manufactured of a substantially flexible material which allows them to extend through the tubing channels 40 and out the apertures 30 to reach the fallopian tubes. The tubes 60 may alternatively be manufactured of different materials with the part of the tubes 60 extending through the tubing channels 40 being of a flexible material and the part of the tubes 60 extending into the working space 47 being of a more rigid material to ensure that the tubing 60 fully extends through the tubing channels 40 without the tubes 60 collapsing at the entrance to the tubing channels 40.

The first opposing end of the inserter 20 containing the first flange 45 has a first opening 46 disposed therein into which the cylindrical chamber 50 is inserted. This first opening 46 is of sufficient dimension so as to allow the comfortable insertion of the cylindrical chamber 50 into the tubular inserter 20.

The tubular inserter 20 is manufactured of a biocompatible material and has a smooth exterior to facilitate entry into the vagina and uterus. Types of biocompatible materials that can be used to manufacture the device 10 include biocompatible plastics such as a thermoplastic material or an ABS plastic that can be injection molded to precise specifications.

The tubular inserter 20 can be manufactured in a shape similar to a tampon for easy insertion. The tubular inserter 20 is of sufficient dimension so as to fit adequately into various sized female reproductive systems through the vagina and into the uterus. Average, minimum and maximum dimensions of female reproductive systems were collected to determine the appropriate dimensions for the device. The size of the device 10 is designed to minimize the patient's discomfort during insertion and does not damage the female reproductive organs internally. The dimensions of the uterus for women who have not had children are approximately 7.5 cm in length, 5 cm in depth, and 2.5 cm in thickness. The length of the vagina from the cervix ranges from 8 to 10 cm. The portion attached to the uterus known as the isthmus is about 1 cm in length and about 1 mm in internal diameter. These dimensions are considered the normal average for uterus size.

The cylindrical chamber 50 is a hollow elongated tube designed to fit within the tubular inserter 20. The chamber 50 is of sufficient length to reach only the farthest end of the working space 47 adjacent to the entrance to the tubing channels 40 of the tubular inserter 20. The chamber 50 functions to control the length of tubing 60 which extends through the tubing channels 40 and out the apertures 30 to reach the entrance of the fallopian tubes.

The second insertion end of the chamber 50 can be substantially closed or depending on the embodiment may be open to allow the tubes 60 to pass through to the tubing channels 40. This end can have a one or a plurality of small openings through which the agent 90 can be released into the tubes 60. Alternatively, the second insertion end of the chamber 50 can have tubes attached which then extend into the tubing channels 40 of the inserter 20. The second opposing end of the chamber 50 contains a second flange 65 having a second opening 66 disposed therein for the insertion of the plunger 70.

The plunger 70 is an elongated solid cylinder designed to fit within the chamber 50. The plunger 70 is of sufficient length to reach the second insertion end of the chamber 50. In an embodiment, the plunger 70 may act as a syringe to push the agent 90 through the chamber 50 and into the tubes 60.

In an alternative embodiment, the third insertion end of the plunger 70 can contain a dispensing compartment 80 into which an agent 90 such as a drug or semen can be contained for delivery. The dispensing compartment 80 is manufactured of a material which allows for the release of the agent 90 upon the contact of the dispensing compartment 80 with the second insertion end of the chamber 50. In an embodiment, the dispensing compartment 80 is manufactured of a material which collapses upon contact with the insertion end of the chamber 50 thus releasing the agent 90 into the tubes 60. In an alternative embodiment, the dispensing chamber 50 may have an opening which releases the agent 90 upon contact with the second insertion end of the chamber 50. The third opposing end of the plunger 70 contains a third flange 85 which functions to control the amount of agent 90 released from the dispensing compartment 80.

Figure 8:
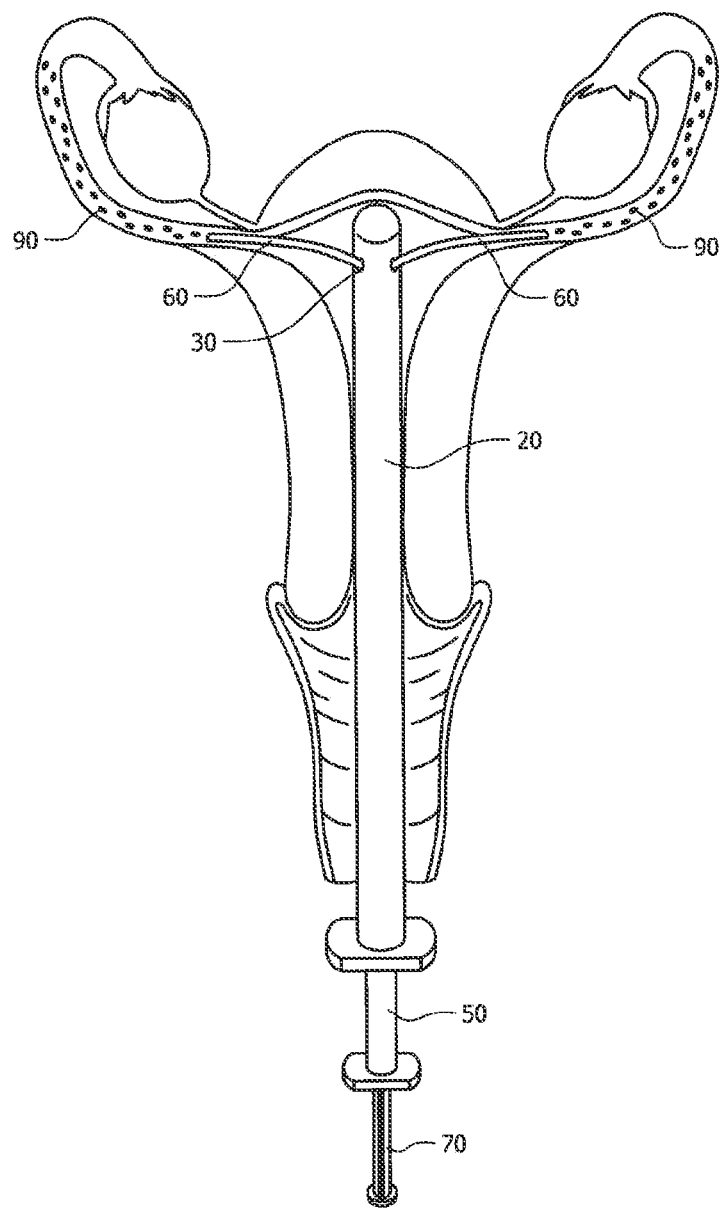
FIG. 8 is an image depicting the device in use as inserted into the uterus of a female. The device is inserted through the vagina into the uterus using ultrasound to position the device correctly in the uterus. The chamber is telescopically extended through the tubular inserter to extend the tubes through the tubing channels and outwardly from the apertures in the tubular inserter. Ultrasound is used to correctly position each tube at the entrance of each fallopian tube. The plunger is then telescopically extended through the chamber until the dispensing compartment is in contact with the insertion end of the chamber. When the dispensing compartment contacts the insertion end of the chamber, the agent contained therein is released into the tubes and travels through the tubes into the fallopian tubes and ultimately the ovaries.

FIG. 8 depicts one embodiment of the device 10 in use in the female reproductive tract. Generally the tubular inserter 20 of the device 10 is inserted through the vagina of the patient and into the uterus. Positioning of the device 10 centrally in the uterus is accomplished through the use of ultrasound. The chamber 50 is inserted into the tubular inserter 20. Adjusting the length of the chamber 50 inserted into the tubular inserter 20 controls the amount of tubing 60 released from the apertures 30 in the tubular inserter 20. Ultrasound is used to ensure the proper placement of each tube 60 at the entrance of each fallopian tube. The plunger 70 is inserted into the chamber 50 and adjustment of the plunger 70 controls the amount of the agent 90 released from the dispensing compartment 80.

The agent 90 can be any agent that is capable of producing a therapeutic effect in the female reproductive system including but not limited to semen for a targeted insemination or a drug used for any purpose ranging from reducing inflammation and infection to treating cancer. The drug can be in any form capable of being contained within the dispensing compartment such as a gel, cream, liquid containing nano-encapsulated drug particles.

In alternative embodiments, the tubular inserter 20 may have one or a plurality of apertures 30 through which an agent 90 such as semen or a drug can be delivered for targeted delivery to the ovaries, fallopian tubes, or uterus.

The device 10 may also alternatively be comprised only of the tubular inserter 20 and the plunger 70. In this embodiment, the plunger 70 functions both to release the agent 90 as well as to control the length of the tubing 60 released from the tubular inserter 20.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described.

What is claimed is:

1. A drug delivery device comprising:
   a tubular inserter having a first insertion end and a first opposing end wherein a distalmost portion of the first insertion end is rounded and the first opposing end has a first flange disposed thereon;
   a pair of apertures disposed in the first insertion end of the tubular inserter;
   at least one tubing channel disposed within the first insertion end of the tubular inserter wherein the at least one tubing channel terminates at the pair of apertures;
   a pair of tubes disposed in the at least one tubing channel;
   a cylindrical chamber having a second insertion end and a second opposing end having a second flange disposed thereon wherein the cylindrical chamber is slidably received and retained within the first opposing end of the tubular inserter; and
   a plunger having a third insertion end and a third opposing end wherein the plunger is slidably received and retained within the second opposing end of the cylindrical chamber.

2. The drug delivery device of claim 1 further comprising a tube extension system selected from the group consisting of:
   (a) a full chamber tubing system wherein the pair of tubes is disposed on the second flange of the cylindrical chamber and extend through the chamber and into at least one tubing channel;
   (b) a reinforced tubing extension system, further comprising a section of the pair of tubes extending from the at least one tubing channel wherein the section of the pair of tubes is substantially rigid and can contact the second insertion end of the chamber;

(c) a disc extension system, further comprising
  a disc having a first side and a second side;
  a pair of apertures extending from the first side of the disc to the second side of the disc;
  a pair of tubes extending from the apertures on the second side of the disc into the at least one tubing channel;
  wherein the second side of the disc is in contact with the second insertion end of the chamber; and
(d) a cylindrical chamber tube extension system, wherein the pair of tubes is disposed on the second insertion end of the cylindrical chamber.

3. The drug delivery device of claim 1 further comprising a first opening in the first flange to receive the second insertion end of the chamber.

4. The drug delivery device of claim 1 further comprising a second opening in the second flange to receive the third insertion end of the plunger.

5. The drug delivery device of claim 1 further comprising a dispensing compartment disposed at the third insertion end of the plunger.

6. The drug delivery device of claim 1 wherein the pair of tubes is substantially longer in length than the at least one tubing channel.

7. The drug delivery device of claim 1 wherein the tubular inserter is cylindrical.

8. The drug device of claim 1 wherein the apertures are positioned on opposing sides of the first insertion end of the tubular inserter.

9. A drug delivery device comprising:
  a tubular inserter having a first insertion end and a first opposing end wherein a distalmost portion of the first insertion end is rounded and the first opposing end has a first flange disposed thereon;
  a pair of apertures disposed in the first insertion end of the tubular inserter;
  a pair of tubing channels disposed within the first insertion end of the tubular inserter wherein each of the tubing channels terminates at one of the apertures;
  a pair of tubes wherein each tube is disposed in one of the tubing channels;
  a cylindrical chamber having a second insertion end and a second opposing end having a second flange disposed thereon wherein the chamber is slidably received and retained within the first opposing end of the tubular inserter; and
  a plunger having a third insertion end and a third opposing end wherein the plunger is slidably received and retained within the second opposing end of the cylindrical chamber.

10. The drug delivery device of claim 9 further comprising a tube extension system selected from the group consisting of:
  (a) a full chamber tubing system wherein the pair of tubes is disposed on the second flange of the cylindrical chamber and extend through the chamber and into the tubing channels;
  (b) a reinforced tubing extension system, further comprising
    a section of the pair of tubes extending from the pair of tubing channels wherein the section of the pair of tubes is substantially rigid and can contact the second insertion end of the chamber;
  (c) a disc extension system, further comprising
    a disc having a first side and a second side;
    a pair of apertures extending from the first side of the disc to the second side of the disc;
    a pair of tubes extending from the apertures on the second side of the disc into the pair of tubing channels;
    wherein the second side of the disc is in contact with the second insertion end of the chamber; and
  (d) a cylindrical chamber tube extension system, wherein the pair of tubes is disposed on the second insertion end of the cylindrical chamber.

11. The drug delivery device of claim 9 further comprising a first opening in the first flange to receive the second insertion end of the chamber.

12. The drug delivery device of claim 9 further comprising a second opening in the second flange to receive the third insertion end of the plunger.

13. The drug delivery device of claim 9 further comprising a dispensing compartment disposed at the third insertion end of the plunger.

14. The drug delivery device of claim 9 wherein the pair of tubes is substantially longer in length than the pair of tubing channels.

15. The drug delivery device of claim 9 wherein the tubular inserter is cylindrical.

16. The drug device of claim 9 wherein the apertures are positioned on opposing sides of the first insertion end of the tubular inserter.

17. A drug delivery system comprising:
  a drug delivery device comprising:
    a tubular inserter having a first insertion end and a first opposing end wherein a distalmost portion of the first insertion end is rounded and the first opposing end has a first flange disposed thereon;
    a pair of apertures disposed in the first insertion end of the tubular inserter;
    at least one tubing channel disposed within the first insertion end of the tubular inserter wherein the at least one tubing channel terminates at the pair of apertures;
    a pair of tubes disposed in the at least one tubing channel;
    a cylindrical chamber having a second insertion end and a second opposing end having a second flange disposed thereon wherein the cylindrical chamber is slidably received and retained within the first opposing end of the tubular inserter; and
    a plunger having a third insertion end and a third opposing end wherein the plunger is slidably received and retained within the second opposing end of the cylindrical chamber;
  an ultrasound device;
  an agent; and
  wherein the ultrasound device is used to position the drug delivery device in the uterus and the drug delivery device is used to release the therapeutic agent into the reproductive system.

18. The drug delivery device of claim 17 further comprising a tube extension system selected from the group consisting of:
  (a) a full chamber tubing system wherein the pair of tubes is disposed on the second flange of the cylindrical chamber and extend through the chamber and into at least one tubing channel;
  (b) a reinforced tubing extension system, further comprising
    a section of the pair of tubes extending from the at least one tubing channel wherein the section of the pair of tubes is substantially rigid and can contact the second insertion end of the chamber;

(c) a disc extension system, further comprising
   a disc having a first side and a second side;
   a pair of apertures extending from the first side of the disc to the second side of the disc;
   a pair of tubes extending from the apertures on the second side of the disc into the at least one tubing channel;
   wherein the second side of the disc is in contact with the second insertion end of the chamber; and
(d) a cylindrical chamber tube extension system, wherein the pair of tubes is disposed on the second insertion end of the cylindrical chamber.

19. The drug delivery device of claim 17 further comprising a dispensing compartment disposed at the third insertion end of the plunger.

20. The drug delivery device of claim 17 wherein the pair of tubes is substantially longer in length than the at least one tubing channel.

\* \* \* \* \*